(12) United States Patent
Hindley et al.

(10) Patent No.: US 10,849,839 B2
(45) Date of Patent: Dec. 1, 2020

(54) PERSONAL CARE COMPOSITIONS

(75) Inventors: Michael Christopher Hindley, Yorkshire (GB); David John Freeman, East Yorkshire (GB); James Prodger, Yorkshire (GB); Sean Philip Nigel Rouse, Yorkshire (GB)

(73) Assignee: Croda International Plc (GB)

( * ) Notice: Subject to any disclaimer, the term of this patent is extended or adjusted under 35 U.S.C. 154(b) by 0 days.

(21) Appl. No.: 14/130,609

(22) PCT Filed: Jul. 3, 2012

(86) PCT No.: PCT/GB2012/051551
§ 371 (c)(1),
(2), (4) Date: Feb. 27, 2014

(87) PCT Pub. No.: WO2013/005025
PCT Pub. Date: Jan. 10, 2013

(65) Prior Publication Data
US 2014/0199253 A1    Jul. 17, 2014

(30) Foreign Application Priority Data

Jul. 6, 2011 (GB) .................................. 1111543.3

(51) Int. Cl.
| | |
|---|---|
| A61K 8/44 | (2006.01) |
| A61Q 5/00 | (2006.01) |
| A61K 8/84 | (2006.01) |
| A61Q 5/12 | (2006.01) |
| A61K 8/42 | (2006.01) |

(52) U.S. Cl.
CPC ................ *A61K 8/442* (2013.01); *A61K 8/42* (2013.01); *A61K 8/84* (2013.01); *A61Q 5/00* (2013.01); *A61Q 5/002* (2013.01); *A61Q 5/12* (2013.01)

(58) Field of Classification Search
None
See application file for complete search history.

(56) References Cited

U.S. PATENT DOCUMENTS

| | | | |
|---|---|---|---|
| 5,041,553 A * | 8/1991 | Keil | C07D 233/16 548/349.1 |
| 6,579,846 B1 | 6/2003 | Zirnstein | |
| 2003/0103926 A1 | 6/2003 | Maubru | |
| 2003/0103927 A1 | 6/2003 | Maubru | |
| 2003/0108503 A1 | 6/2003 | Maubru et al. | |
| 2003/0130162 A1 | 7/2003 | Llosas | |
| 2004/0001796 A9 | 1/2004 | Maubru | |
| 2004/0146478 A1 | 7/2004 | Queralt | |
| 2009/0169502 A1* | 7/2009 | Quadir | A61K 8/36 424/70.9 |
| 2010/0203003 A1 | 8/2010 | Kokeguchi et al. | |
| 2010/0317554 A1 | 12/2010 | Fuchi et al. | |

FOREIGN PATENT DOCUMENTS

| | | |
|---|---|---|
| EP | 1500744 | 1/2005 |
| JP | 7138555 | 5/1995 |
| JP | 2000178145 | 6/2000 |
| JP | 2000204160 | 7/2000 |
| JP | 2003081776 | 3/2003 |
| JP | 2003519294 | 6/2003 |
| JP | 2004527550 | 9/2004 |
| JP | 2004285521 | 10/2004 |
| JP | 2010 077061 A | 4/2010 |
| JP | 20111406 | 1/2011 |
| WO | WO 2006/016549 | 2/2006 |
| WO | WO 2009/053686 A1 | 4/2009 |

OTHER PUBLICATIONS

English translation of Tomokazu (JP 2010077061).*
International Search Report for WO2013/005025 (PCT/GB2012/051551).
Notice of Reasons for Rejection for Japanese Application No. 2014517949, dated Feb. 9, 2016, 4 pages.
English translation of JP Office Action dated Nov. 15, 2016, 5 pages.

* cited by examiner

*Primary Examiner* — Patricia Duffy
*Assistant Examiner* — Garen Gotfredson
(74) *Attorney, Agent, or Firm* — RatnerPrestia

(57) ABSTRACT

A personal care formulation comprising an active compound is operable to reduce the surface friction of hair fibres and promoting inter-fibre movement. The active compound is the reaction product of a fatty acid and a polyamine. The use of the active compound in a personal care formulation works as a friction modifier operable to reduce the surface friction of hair fibres. The invention extends to the active compound and a method of reducing hair-fibre surface friction.

13 Claims, 3 Drawing Sheets

PERSONAL CARE COMPOSITIONS

CROSS REFERENCE TO RELATED APPLICATIONS

This application is the U.S. National Phase application of PCT International Application No. PCT/GB2012/051551, filed Jul. 3, 2012, and claims priority of British Patent Application No. 1111543.3, filed Jul. 6, 2011, the disclosures of which are incorporated herein by reference in their entireties for all purposes.

FIELD OF THE INVENTION

The present invention relates to a personal care composition, more particularly to a hair care composition. In particular, the present invention relates to a composition for promoting healthy looking hair and/or skin. The composition is particularly effective in reducing the surface friction of hair fibres, allowing strands of hair to move freely over one another.

BACKGROUND OF THE INVENTION

The practice of bleaching, colouring or dying hair is in common use by women and men. Bleaching is a permanent alteration of the hair. Hair bleaches are commonly used to lighten the colour of hair fibres through the oxidation of melanin pigments within the hair. Melanin is mainly contained within the outer layers of the hair and less so in the cortex. Oxidising agents such as hydrogen peroxide are used to oxidise the melanin, which effectively destroys the pigment. However, the peroxide alone does not result in a colour change and accelerators or promoters such as ammonium or potassium persulphate are used. These help the peroxide to oxidise the melanin pigments. These systems are generally formulated to a high pH of around 9 as the decomposition of peroxide is optimal at this pH.

Hair colours or dyes can be permanent, semi-permanent or temporary depending on the user's desired result. Permanent and semi-permanent hair dyes comprise pigment molecules which penetrate the hair to hold the colour within the hair itself, whilst the pigment molecules in temporary hair dyes merely adsorb or adhere onto the hair surface.

The most popular way to achieve permanent or semi-permanent hair colouring is through the use of oxidation, or oxidative, dyes. Such dyes use an oxidant under extreme basic conditions to penetrate the hair. Similarly to hair bleaches, in hair dyes, typically hydrogen peroxide is used as the oxidant, and ammonia, sodium hydroxide, or the like, is used as a promoter or accelerant for the oxidation process. The hydrogen peroxide oxidation of the hair's natural melanin provides a blank canvas for the dye.

The conditions provided by hair bleaches and dyes are well documented to cause damage to the hair fibre, resulting in weakened fibres and high levels of inter-fibre friction. This occurs due to the bleaching/dying systems causing the removal of the layer of covalently bound surface lipid 18-MEA (18-methyl eicosenoic acid). This lipid layer is responsible for protecting the hair, helping it to remain hydrophobic and helping to keep the hair smooth and untangled. The peroxide, persulphate and high pH can also result in cuticle lifting which adds to the problem of friction between fibres.

Undamaged hair, often referred to as 'healthy hair' or, more accurately, 'healthy-looking hair' is desirable for all individuals and returning hair to this state after it has been subjected to damaging cosmetic treatments has been the goal of many hair care products.

Traditionally, products that have been available to 'restore' the 'healthy-looking' state of hair after bleaching or colouring treatments are based on quaternised materials, such as for example, behentrimonium chloride and/or cetearyl ethylhexyldimonium methosulfate. However, quaternised materials are disadvantageous in that they have been associated with a range of adverse health effects, including skin and respiratory irritation.

Silicones, such as dimethicone, have also been used widely in such products, and have also been associated with negative environmental effects. Furthermore, silicones can "build-up" in the hair and be difficult to remove using surfactants of the type used in shampoos.

There exists, therefore, a need for a product which negates the disadvantages associated with quaternised and/or silicone materials.

One property of so-called 'healthy hair' is its increased ability to move freely under the natural motion of moving ones head. Damaged hair, such as bleached or colour treated hair, has a reduced ability to move due to higher levels of inter-fibre friction caused by the damaging cosmetic treatments.

There exists also, therefore, a need for a product which restores and/or improves the hair's natural ability to move, and reduces inter-fibre friction, especially in cosmetically treated hair.

SUMMARY OF THE INVENTION

It is an object of the present invention to address the above and other disadvantages associated with the prior art.

Thus, according to a first aspect of the present invention, there is provided a personal care formulation comprising an active compound which is the reaction product of a fatty acid and a polyamine.

According to a second aspect of the present invention, there is provided a personal care formulation for reducing the surface friction of hair fibres and promoting inter-fibre movement, the formulation comprising the active compound of the first aspect of the invention.

DETAILED DESCRIPTION OF THE INVENTION

Figure 1:
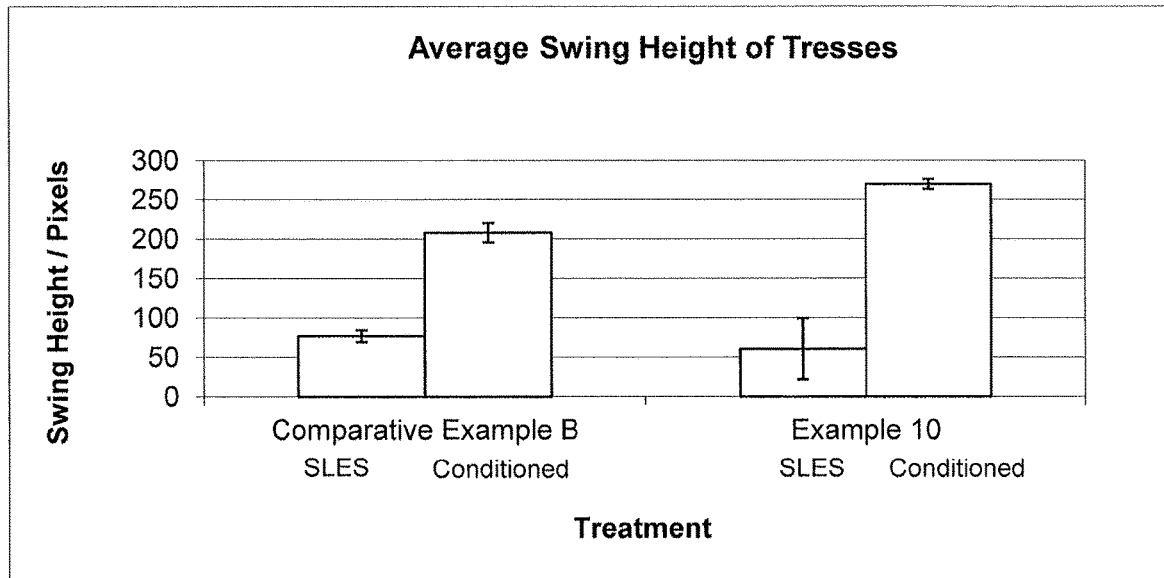
FIG. 1 is a graph of the calculated swing height of bleach damaged tresses washed with SLES only compared to tresses conditioned with either Comparative Example B or Example 10.

The personal care formulation comprising an active compound which is the reaction product of a fatty acid and a polyamine may be a skin care or hair care formulation.

Preferably, the personal care formulation is a hair care formulation. More preferably, the personal care formulation is a hair cleansing, conditioning, de-tangling, colour-protecting or styling formulation. More preferably, the personal care formulation is a friction modifying formulation operable to reduce the surface friction of human or animal hair fibres.

By the use of the term "active compound" in the present specification, it is meant a compound which has an effect on a substrate. Preferably, the reaction product of the fatty acid and polyamine is a friction modifier, operable to reduce the surface friction of the hair or skin, preferably of hair fibres.

By the use of the term "polyamine" in the present specification, it is meant a compound comprising two or more amine groups, preferably three or more amine groups. The amine groups present in the polyamine may be independently primary, secondary or tertiary. Preferably, the terminal amine groups in the polyamine are primary and the remainder of the amine groups secondary/tertiary.

By the use of the term "fatty acid" in the present specification, it is meant a carboxylic acid having a long carbon chain of between 12 and 30 carbon atoms, preferably between 16 and 26, more preferably between 18 and 22 carbon atoms.

Preferably, the active compound is a fatty amino-amide/ester, more preferably, a mixture of fatty amino-amides/esters.

The fatty acid may be either a branched fatty acid or a linear fatty acid. A mixture of fatty acids may be present in the formulation of the invention. In this case, the mixture may comprise branched fatty acids, linear fatty acids, or a mixture thereof.

Preferably, the fatty acid is a branched fatty acid. The branched fatty acid preferably comprises alkyl side branches (attached directly to a carbon atom of the longest linear chain) having on average less than 3, more preferably less than 2.5, particularly in the range from 1.05 to 2, and especially 1.1 to 1.4 carbon atoms, i.e. the side branches are predominantly methyl groups.

Suitable branched chain fatty acids for use in the present invention include iso-acids such as isostearic acid, isopalmitic acid, isomyristic acid, isoarachidic acid and isobehenic acid; neo-acids such as neodecanioc acid; and/or anti-iso acids. Preferably, the branched chain fatty acid is an iso-acid. Isostearic acid is preferred.

Preferably, the fatty acid has a molecular weight of between 150 and 500 Daltons, preferably between 200 and 400 Daltons, more preferably between 250 and 350 Daltons, and desirably between 270 and 310 Daltons.

Fatty acids suitable for use herein can be obtained from natural sources such as, for example plant or animal esters. For example, the acids may be obtained from palm oil, rape seed oil, palm kernel oil, coconut oil, babassu oil, soybean oil, castor oil, sunflower oil, olive oil, linseed oil, cottonseed oil, safflower oil, tallow, whale or fish oils, grease, lard and mixtures thereof. The fatty acids can also be synthetically prepared. Relatively pure unsaturated fatty acids such as oleic acid, linoleic acid, linolenic acid, palmitoleic acid, and elaidic acid may be isolated, or relatively crude unsaturated fatty acid mixtures employed. Resin acids, such as those present in tall oil, may also be used.

Preferably, the polyamine has the general structure of formula I.

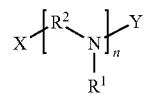

Formula I

Each $R^1$ is preferably a moiety independently selected from the group comprising —H, a lower alkyl group or a lower alkylene group operable to bond with another N atom in the polymer chain. Preferably, each $R^1$ is either H or a lower alkylene group, preferably methylene, ethylene or propylene, operable to bond with another N atom, preferably the N atom of an adjacent repeating unit, in the polymer chain, more preferably H. The $R^1$ moieties may be the same as each other or different from each other. Preferably, all the $R^1$ moieties are the same as each other.

Each $R^2$ is independently preferably a lower alkylene moiety, preferably a methylene, ethylene, propylene or butylene moiety, more preferably a methylene or ethylene moiety, most preferably an ethylene moiety. Each of the $R^2$ moieties may be the same as each other or different from each other. Preferably, all the $R^2$ moieties are the same as each other.

X is preferably the moiety —$NR^3_2$, wherein each $R^3$ moiety is independently selected from the group comprising H and lower alkyl. X is preferably —$NH_2$.

Y is preferably the moiety —$R^4$, wherein $R^4$ is selected from the group comprising H and lower alkyl. Y is preferably —H.

The $R^3$ and $R^4$ moieties may be the same as each other or different from each other. Preferably, all the $R^3$ and $R^4$ moieties are the same as each other.

n is preferably an integer between 1 and 20, preferably between 1 and 12, more preferably between 2 and 8 and most preferably between 3 and 5.

By the use of the term "lower alkylene" in the present specification, it is meant any moiety having the general structure —$C_mH_{2m+1}$, wherein m is an integer between 1 and 20, preferably between 1 and 15, preferably between 1 and 10 and most preferably between 1 and 6

By the use of the term "lower alkyl" in the present specification, it is meant any moiety having the general structure —$C_mH_{2m+1}$, wherein m is an integer between 1 and 20, preferably between 1 and 15, preferably between 1 and 10 and most preferably between 1 and 6

Preferably, the polyamine of the invention has a molecular weight of up to 1000 Daltons, preferably up to 700 Daltons, more preferably up to 500 Daltons and most preferably up to 300 Daltons, and of at least 50 Daltons, more preferably at least 100 Daltons, most preferably at least 150 Daltons.

The polyamine may be linear or branched. Preferably, the polyamine is a linear polyamine. Preferably, each $R^1$, $R^3$ and $R^4$ in formula I is H.

The polyamine may comprise one or more cyclic moieties. Cyclic moieties may be present in either linear or branched polyamines. Preferably, cyclic moieties in the polyamines are effected when an $R^1$ group is a lower alkylene moiety and bonds to another N atom in the polymer chain, preferably an N atom in an adjacent repeating unit of the polyamine. Preferably, when the polyamine comprises a cyclic moiety, it is a piperazine moiety. Alternatively, cyclic moieties may be formed from cross-linking between $R^1$, $R^2$, $R^3$ and/or $R^4$ groups, preferably between $R^1$ and $R^2$ moieties.

Preferably, the polyamine of has a general formula $NH_2(CH_2CH_2NH)_nH$.

Preferably, the polyamine of the first embodiment of the invention is an alkyleneamine or oligoalkyleneamine. Examples of suitable alkyleneamines or oligoalkyleneamines include diethylene triamine, triethylene tetramine, tetraethylene pentamine, pentaethylene hexamine. Preferably, the polyamine is a tetraethylene pentamine.

A mixture of polyamines may be present in the active compound of the invention. In this case, the mixture may comprise branched polyamines, linear polyamines, or a mixture thereof.

Preferably, the mol ratio of fatty acid to polyamine in the reaction product is at least 0.01:1, preferably at least 0.5:1, more preferably at least 1:1 and most preferably at least 2:1.

Preferably, the mol ratio of fatty acid to polyamine in the reaction product is up to 10:1, preferably up to 8:1, more preferably up to 6:1 and most preferably up to 4:1.

The reaction product of the fatty acid and the polyamine may be symmetric or asymmetric.

Furthermore, mixtures of reaction products may be formed. Such mixtures may comprise symmetric compounds, asymmetric compounds or mixtures of the two. Preferably, the reaction product comprises symmetric compounds. More preferably, the reaction product is free from asymmetric compounds.

Preferably, the mol ratio of fatty acid to polyamine increases as the molecular weight of the polyamine increases.

Preferably, the active compound is anhydrous. By the term anhydrous, it is meant that the compound preferably comprises a maximum of 10% by weight water. More preferably, the active compound comprises a maximum of 7% by weight water, most preferably, 5% and desirably 2% by weight. Preferably, the compound comprises 0.01% to 10% by weight water, preferably 0.05% to 5%, most preferably 0.1% to 2% by weight.

Preferably, the active compound is a personal care active compound, preferably a hair care active compound, preferably a hair conditioning agent, more preferably a hair-fibre friction modifier. Preferably, the active compound is a conditioning agent, preferably a friction modifier.

Preferably, the active compound is present at a low concentration in the personal care formulation. Preferably, the active compound is present in the formulation at a concentration of at least 0.01% w/w, preferably at least 0.1% w/w, more preferably at least 0.5% w/w and most preferably at least 0.8% w/w based on the total weight of the formulation. Preferably, the active compound is present in the formulation at a concentration of up to 5% w/w, preferably up to 4% w/w, more preferably up to 3% w/w and most preferably up to 2% w/w based on the total weight of the formulation.

Preferably, the personal care formulation further comprises a base vehicle to carry the active compound. Preferably, the vehicle comprises a relatively high concentration of water. Preferably, water is present in the personal care formulation at a concentration of at least 20% w/w, preferably at least 25% w/w, more preferably at least 28% w/w and most preferably at least 30% w/w of the total formulation. Preferably, water is present in the personal care formulation at a concentration of up to 99.9% w/w, preferably up to 99% w/w, preferably, up to 98% w/w and most preferably up to 97% w/w of the total formulation.

Preferably, the personal care formulation is acidic. Preferably the formulation has a pH of between 1 and 6, preferably between 2 and 5.5, more preferably of between 3 and 5, and most preferably of between 4 and 4.5.

The personal care formulations of the type defined herein may be in the form of oil in water emulsions; water in oil emulsions; anhydrous formulations, including massage oils, hair sprays/serums; detergent formulations; more particularly in personal care emulsion formulations such as oil in water emulsions and detergent formulations. Personal care emulsion formulations can take the form of pastes, creams, liquids and milks desirably, and in the field of hair care formulations aim to provide a pleasant aesthetic feel to the hair as well as improving manageability and visual appearance.

The personal care formulation may have a range of different consistencies and/or viscosities depending on the desired end use of the formulation.

When the personal care formulation has a viscosity of a conditioner, for example a cream emulsion, preferably a dropping consistency cream emulsion, the viscosity of the formulation is preferably at least 4000 Pa·s, preferably at least 5000 Pa·s, more preferably at least 6000 Pa·s and most preferably at least 8000 Pa·s at 25° C. and 1 atmosphere pressure. Preferably in this case, the viscosity of the formulation is up to 80,000 Pa·s, preferably up to 50,000 Pa·s, more preferably up to 25,000 Pa·s and most preferably up to 10,000 Pa·s at 25° C. and 1 atmosphere pressure.

When the personal care formulation has a viscosity of a shampoo for example, the viscosity of the formulation is preferably at least 500 cps, preferably at least 800 cps, more preferably at least 1000 cps and most preferably at least 1500 cps at 25° C. and 1 atmosphere pressure. Preferably in this case, the viscosity of the formulation is up to 10000 cps, preferably up to 8000 cps, more preferably up to 5000 cps and most preferably up to 4000 cps at 25° C. and 1 atmosphere pressure.

When the personal care formulation has a viscosity of a serum for example, the viscosity of the formulation is preferably at least 300 cps, preferably at least 500 cps, more preferably at least 800 cps and most preferably at least 1000 cps at 25° C. and 1 atmosphere pressure. Preferably in this case, the viscosity of the formulation is up to 10000 cps, preferably up to 8000 cps, more preferably up to 5000 cps and most preferably up to 3000 cps at 25° C. and 1 atmosphere pressure.

When the personal care formulation has a viscosity of an oil for example, the viscosity of the formulation is preferably at least 30 cps, preferably at least 50 cps, more preferably at least 80 cps and most preferably at least 100 cps at 25° C. and 1 atmosphere pressure. Preferably in this case, the viscosity of the formulation is up to 1000 cps, preferably up to 500 cps, more preferably up to 400 cps and most preferably up to 300 cps at 25° C. and 1 atmosphere pressure.

When the personal care formulation has a viscosity of a hair spray for example, the viscosity of the formulation is preferably at least 1 cps, preferably at least 5 cps, more preferably at least 8 cps and most preferably at least 1 cps at 25° C. and 1 atmosphere pressure. Preferably in this case, the viscosity of the formulation is up to 500 cps, preferably up to 400 cps, more preferably up to 300 cps and most preferably up to 200 cps at 25° C. and 1 atmosphere pressure.

The end use applications of such formulations include, in the field of personal care products, moisturizers, body butters, gel creams, high perfume containing products, perfume creams, hair conditioners, hair relaxer formulations, hair shampoos, hair styling products, leave-on hair products, water-free products, anti-perspirant and deodorant products, cleansers, 2-in-1 foaming emulsions, emulsifier free products, mild formulations, scrub formulations e.g. containing solid beads, silicone in water formulations, pigment containing products, sprayable emulsions, colour cosmetics, shower products, make-up remover, eye make-up remover, and wipes.

Personal care emulsion formulations comprising the active compounds of the present invention may include various other personal care ingredients. For example, suitable other ingredients include one or more ingredients such as cleansing agents, hair conditioning agents, skin conditioning agents, hair styling agents, antidandruff agents, hair growth promoters, perfumes, sunscreen compounds, pigments, moisturizers, film formers, humectants, alpha-hydroxy acids, hair colours, make-up agents, detergents, thickening agents, antiseptic agents, deodorant actives and surfactants.

Preferably, no further active conditioning ingredients are needed in the personal care formulation. Preferably the active compound which is the reaction product of a fatty acid and a polyamine is the only active conditioning ingredient present in the formulation. Preferably, the formulation is free from additional conditioning components, for example quaternised materials or silicones.

The personal care formulation may comprise additional components, for example, additional emollients, carriers, surfactants and the like.

Preferably, the personal care formulation further comprises an emulsifier. Preferably, the emulsifier is a non-ionic, high HLB (hydrophilic/lipophillic balance) surfactant which is capable of forming an oil-in-water emulsion. Preferably, the emulsifier is naturally derived. Examples of suitable emulsifiers include ethoxylated sorbitan esters, ethoxylated glyceryl esters, ethoxylated fatty alcohols (including lanolin alcohols), ethoxylated fatty acids (including lanolin fatty acids), glycerol fatty acid mono-esters, glycol fatty acid mono and di-esters, sugar esters (fatty acid mono and di esters of sucrose), fatty acid polyol (polyethylene glycol) esters and fatty alcohols (which may also act as co-emulsifiers). Preferably, the emulsifier is an alkoxylated alcohol, preferably an alcohol ethoxylate. Particularly preferred emulsifiers include polyoxyethylene (20) stearyl ether (commercially available as Brij S20 ex Croda).

When present in the formulation, the emulsifier is preferably present at a concentration of at least 0.2% w/w, preferably at least 0.5% w/w, more preferably at least 0.9% w/w and most preferably at least 1.1% w/w based on the total weight of the formulation. Preferably, the emulsifier is present in the formulation at a concentration of up to 20% w/w, preferably up to 12% w/w, more preferably up to 7% w/w and most preferably up to 5% w/w based on the total weight of the formulation. The concentration of emulsifier present in the formulation is preferably higher than that present in a formulation of this type comprising quaternised materials. This is to compensate for the absence of quaternised materials in the formulation which would usually have an emulsifying effect on the formulation.

The personal care formulation may further comprise at least one co-emulsifier. Preferably, the or each co-emulsifier is a viscosity modifier, able to modify the viscosity of the formulation, more preferably a viscosity builder, able to increase the viscosity of the formulation. Preferably, the or each co-emulsifier is a fatty alcohol, preferably a $C_{12}$ to $C_{20}$ alcohol, more preferably a $C_{16}$ to $C_{18}$ alcohol, or a mixture thereof. Suitable alcohols for use as co-emulsifiers in the personal care formulation include cetyl alcohol, stearyl alcohol and cetearyl alcohol.

The formulations according to the present invention may also contain other additional emollient materials, preferably emollient oils. Preferably, the emollient oil is a non-polar oil. Examples of emollient oils which are suitable for use in the present formulation include mineral or paraffin oil; esters of fatty acids and fatty alcohols, preferably $C_{10}$-$C_{20}$ acids or alcohols, although isopropyl esters may be used; fatty acid glycol esters; fatty acid triglycerides; esters and diesters of alkoxylated fatty alcohols; botanical (plant) extracts; and hydrocarbons, preferably $C_{12}$-$C_{16}$. Preferably, the emollient is mineral oil. When present in the formulation, the or each additional emollient is preferably present at a concentration of at least 1% and up to 30% by weight based on the total weight of the formulation.

The personal care formulation according to the present invention may also contain one or more surfactants, for example sodium lauryl ether sulphate or cocamidopropyl betaine. When present in the formulation, the or each surfactant is preferably present at a concentration of between 1% and 20%, preferably between 2% and 15% and more preferably between 4% and 10% by weight based on the total weight of the formulation.

The personal care formulation according to the present invention may also contain one or more proteins or derivatised proteins. When present in the formulation, the or each protein or derivatised protein is preferably present at a concentration of between 0.1% and 10%, preferably between 0.5% and 8% and more preferably between 1% and 5% by weight based on the total weight of the formulation.

The personal care formulation according to the present invention may also contain one or more cationic ingredients. When present in the formulation, the or each cationic ingredient is preferably present at a concentration of between 0.01% and 10%, preferably between 0.05% and 8% and more preferably between 0.1% and 5% by weight based on the total weight of the formulation.

The personal care formulation according to the present invention may also contain one or more silicones. When present in the formulation, the or each slicone is preferably present at a concentration of between 0.05% and 10%, preferably between 0.1% and 8% and more preferably between 0.5% and 5% by weight based on the total weight of the formulation.

The personal care formulation according to the present invention may also contain one or more film forming components. When present in the formulation, the or each film forming component is preferably present at a concentration of between 0.01% and 5%, preferably between 0.05% and 3% and more preferably between 0.1% and 2% by weight based on the total weight of the formulation.

The present invention further extends to the use of the active compound according to the first and/or second aspect of the present invention in a personal care formulation as a friction modifier operable to reduce the surface friction of hair fibres.

According to a third aspect of the present invention there is provided a personal care active compound comprising the reaction product of a fatty acid and a polyamine as described in the first and/or second aspect of the invention.

According to a fourth aspect of the present invention, there is provided a method of reducing hair-fibre surface friction, the method comprising applying to the hair of an individual an effective amount of an active compound according to the first aspect and/or second of the invention.

Preferably, the active compound of the first and/or second aspect of the invention is applied to the hair in a personal care formulation further comprising a base vehicle according to the first and/or second aspect of the invention.

Any of the above features may be taken in any combination and with any aspect of the invention.

EXAMPLES

The present invention will now be described further, for illustrative purposes only, in the following examples. All parts and percentages are given by weight unless otherwise stated.

Active Compound Synthesis Examples

Example 1

Isostearic acid (FA1) (commercially available ex Croda, approx MW 300 Da) (300 g, 1.00 mol) was heated in a reaction vessel to 90° C. before adding tetraethylene pentamine (AM1) (commercially available ex Huntsman, approx molecular weight 200 Da) (95.2 g, 0.476 mol), i.e. a molar ratio of isostearic acid to amine of 2.1:1. The mixture was then heated to 180° C. under nitrogen with constant stirring. The conditions were maintained for the period specified in Table 1 and then the temperature was increased to 225° C. with concomitant use of vacuum for a specified time, as indicated in Table 1, to drive the reaction to completion. After cooling to ambient temperature under nitrogen the product was recovered as a viscous liquid.

Examples 2 to 7

The products of these examples were made by the method described in Example 1 but using the appropriate materials and amounts. The materials, molar ratios used and the reaction conditions for Examples 2 to 7 are summarised in Table 1 below.

TABLE 1

Examples 1 to 7

| Ex. No. | Fatty acid Type | mol | Amine Type | mol | Time at 180° C./h | Time at 225° C./h | Time under vacuum/h |
|---|---|---|---|---|---|---|---|
| 1 | FA1 | 2.1 | AM1 | 1.0 | 3 | 3 | 3 |
| 2 | FA1 | 2.6 | AM1 | 1.0 | 3 | 3 | 0 |
| 3 | FA1 | 2.8 | AM1 | 1.0 | 0 | 4 | 4 |
| 4 | FA1 | 2.8 | AM1 | 1.0 | 4 | 4 | 3 |
| 5 | FA1 | 3.0 | AM1 | 1.0 | 3 | 4.5 | 0 |
| 6 | FA1 | 3.2 | AM1 | 1.0 | 4 | 5 | 4 |
| 7 | FA1 | 4.0 | AM1 | 1.0 | 4 | 4 | 0 |

Example 8

Alternative Synthesis of Higher Molar Ratio of Fatty Acid:Amine

The product from Example 1 (SE1) (250.0 g) and isostearic acid (FA1) (56.3 g) were added to a flask. The mixture was then heated to 180° C. under nitrogen with constant stirring. The conditions were maintained for the time period specified in Table 3 before increasing the temperature to 225° C. with concomitant use of vacuum for a specified time, as indicated in Table 3. After cooling to ambient temperature under nitrogen the product was recovered as a viscous liquid.

Example 9

The product of this example was made by the method described in Example 8 but using appropriate materials and amounts. The materials, effective molar ratios used and the reaction conditions for examples 8 and 9 are summarised in Table 3 below.

TABLE 3

Synthesis Examples 8 and 9

| Ex. No. | Amount SE1/g | FA1/g | Effective molar ratio FA1:AM1 | Time at 180° C./h | Time at 225° C./h | Time under vacuum/h |
|---|---|---|---|---|---|---|
| 8 | 250.0 | 56.3 | 2.7:1 | 2 | 4 | 4 |
| 9 | 250.0 | 62.6 | 2.8:1 | 0 | 5 | 3 |

Properties of Examples 1 to 9

Some properties of the materials synthesised in Examples 1 to 9 are summarised in Table 4 below.

TABLE 4

Properties of Synthesis Examples 1 to 9

| Ex No | Acid value/ mgKOHg$^{-1}$ | Total Amine Value/ mgKOHg$^{-1}$ | Appearance at RT |
|---|---|---|---|
| 1 | 0.5 | 170.7 | Viscous amber liquid |
| 2 | 4.2 | 126.7 | Viscous yellow liquid |
| 3 | 8.2 | 114.7 | Viscous amber liquid |
| 4 | 6.7 | 114.1 | Viscous amber liquid |
| 5 | 7.9 | 97.7 | Viscous yellow liquid |
| 6 | 9.5 | 100.8 | Viscous amber liquid |
| 7 | 21.8 | 52.7 | Viscous yellow liquid |
| 8 | 7.0 | 132.3 | Viscous amber liquid |
| 9 | 7.5 | 122.0 | Viscous amber liquid |

Formulation Examples

Example 10

A hair conditioning formulation was prepared comprising the active compound of Example 2 according to the following formulation in Table 5:

TABLE 5

Example 10

| Ingredient | % w/w |
|---|---|
| Cetyl Alcohol | 1.87 |
| Cetearyl Alcohol | 0.93 |
| Brij S20 | 1.20 |
| Light Mineral Oil | 0.50 |
| Active compound of Example 2 | 1.00 |
| Water | to 100 |
| Lactic Acid | to pH 4-4.5 |

Example 11

A hair shampoo formulation was prepared comprising the active compound of Example 2 according to the following formulation in Table 6:

TABLE 6

Example 11

| Ingredient | % w/w |
| --- | --- |
| Sodium Lauryl Ether Sulphate (28% active) | 36.00 |
| Cocamidopropyl Betaine (30% active) | 13.00 |
| Cocamidopropylamine oxide (30% active) | 7.00 |
| PEG-60 Almond Glycerides (and) PEG-6 Caprylic/Capric Glycerides | 7.00 |
| Active compound of Example 2 | 1.00 |
| PEG-150 Pentaerythrityl Tetrastearate and PPG-2 Hydroxyethyl Cocamide and Water | 1.50 |
| Water | to 100 |
| Lactic Acid | to pH 6 |

Example 12

A leave-on hair spray formulation was prepared comprising the active compound of Example 2 according to the following formulation in Table 7:

TABLE 7

Example 12

| Ingredient | % w/w |
| --- | --- |
| Ethanol | 30.00 |
| Active compound of Example 2 | 1.00 |
| Water | 69.00 |
| Lactic Acid | 0.50 |

Comparative Example A

A vehicle for a hair conditioning formulation was prepared according to the following formulation in Table 8:

TABLE 8

Comparative Example A

| Ingredient | % w/w |
| --- | --- |
| Cetyl Alcohol | 1.87 |
| Cetearyl Alcohol | 0.93 |
| Brij S20 | 1.20 |
| Light Mineral Oil | 0.50 |
| Water | to 100 |
| Lactic Acid | to pH 4-4.5 |

Comparative Example B

A hair conditioner comprising quaternised and silicone compounds, of the kind commercially available from Proctor & Gamble (Pantene Aqualight) comprising the following ingredients (listed in order of decreasing concentration):
Water
Stearyl Alcohol
Cetyl Alcohol
Behentrimonium Chloride
Cetearyl Ethylhexyldimonium Methosulfate
Parfum (Perfuming)
Benzyl Alcohol
Bis-aminopropyl Dimethicone
Isopropyl Alcohol
Disodium EDTA
Panthenol
Panthenyl Ethyl Ether
Butylphenyl Methylpropional
Linalool
Hexyl Cinnamal
L-limonene
Magnesium Nitrate
Methylchloroisothiazolinone
Magnesium Chloride
Methylisothiazolinone Application Examples

Example 13

Hair Movement Test

The formulations of Example 10, and Comparative Examples A and B were tested to determine hair movement properties after application of each formulation.
Experimental
Equipment The movement of hair tresses was produced using the hair dynamics tester (custom made equipment) which comprised of a sliding bar mechanism turned by a high torque stirrer (ZR2000, Heidolph Instruments GmbH, Schwabach, Germany). The hair was attached to the sliding bar by using a bull dog style clip to grip the wax strip at the top of the hair tress.

Hair motion was recorded digitally using a high definition, 1920×1080 pixels, video camera (Sanyo Xacti HD2000, SANYO Europe GmbH SANYO, Hertfordshire). To ensure the video images were clear, a photographic, constant D65 light source was used to project an even diffused light across the hair tress and the background. The video files were then converted to a suitable format to be analysed using OjoSoft File conversion software (available from www.ojosoft.com, correct as of Sep. 16, 2010) and Mencoder AVI File conversion software (available from http://www.mplayerhq.hu/design7/dload.html, correct as of Mar. 14, 2011). The converted video files were then analysed using custom developed software (developed by Centre for Visual Computing, University of Bradford, Bradford).
Materials Wax bound, European, virgin hair swatches, medium brown, 25 cm length, (International Hair Importers and Products, Glendale, N.Y.) were cut to form 50 mm wide tresses.

Where tresses were washed/cleaned, a standard 10% active sodium lauryl ether sulphate (SLES) solution was used for washing.

Bleach damage was caused using a commercially available powder bleach and cream peroxide bleaching system as in Table 9:

TABLE 9

Peroxide Bleach Solution

| Ingredient | % w/w |
| --- | --- |
| Re-Oxide Cream Peroxide (12% w/w) | 66.6 |
| Clynol Viton Powder Bleach | 33.4 |

Tresses were conditioned using the products of Example 10, Comparative Example A and Comparative Example B. The commercially available product of Comparative Example B was used as a positive control.

Methods

Tress Preparation

In the preparation of hair tresses, a standard hair washing and treatment protocol was followed.

To cleanse the hair, tresses were wetted and then 2 ml of 10% active SLES solution applied, massaged for 2 minutes to generate a foamy lather and then rinsed under water at 30° C., flowing at 2.0 L/minute for 1 minute.

On treating the tresses, a note of the dry tress weight was made and used as a measure for the amount of treatment product to be applied. After tresses had been cleansed, the required treatment was applied to the hair at a level of 10% by weight of the dry hair tress. The selected treatment was then massaged into the hair for 2 minutes and then rinsed under water at 30° C., flowing at 2.0 L/minute for 1 minute.

To ensure the fibres in the tress were in their natural configuration before drying, the tresses were slowly dipped three times into a 2 L beaker of warm water. All tresses were allowed to drip dry overnight at standard conditions: 50±5% RH, 21±1° C.

When bleaching tresses to cause damage to the hair, approximately 15 g of the powder bleach mixture was applied initially using a tinting brush and then further by massaging by hand to ensure even coverage along the whole length of the tress. The bleach was left for the maximum recommended time of 40 minutes on virgin hair, by which time the colour of the hair had visibly lightened indicating the bleaching process had been successful. The bleaching product was then removed by rinsing in water and then cleansing using the protocol described above.

Test Method

Once the tresses had been allowed to dry they were loaded, individually, onto the hair dynamics tester. The tresses were agitated by the instrument prior to testing to loosen any clumped fibres which had occurred as part of the drying process. The instrument was reset to the required test speed and the video camera set to record. The instrument was started and the hair's motion recorded over 20 swings, after which the instrument was stopped. The video camera continued to record until 30 seconds had passed to ensure all motion had been captured.

Video File Analysis

After capturing the motion of the hair using the hair dynamics tester, the video files were converted using the above mentioned file conversion software. The converted files were then opened in the hair dynamics video analysis software which automatically recognises the tress and can plot its position within the video frame as the tress moves. The co-ordinates of the swing height were output to a text file which is opened in a spreadsheet where data analysis can be performed.

Results

Two sets of 3 tresses were bleached in preparation for testing as negative control samples. On bleaching the hair, the colour lightened indicating that the bleach had successfully damaged the hair. The texture of the hair had also changed compared to the pre-bleached state, feeling course and rough as expected.

The swing height results for the bleach damaged hair tresses both before and after treatment with the conditioning products of Comparative Example B and Example 10 are shown in FIG. 1. The observed swing heights of the products were as follows in Table 10. The significance compared to Comparative Example B was calculated using a 2-sampled, unpaired Student T-Test.

TABLE 10

| | Observed swing heights | |
|---|---|---|
| Treatment | Comparative Example B | Example 10 |
| SLES | 77 | 60 |
| Conditioned | 208 | 269 |

The swing heights observed between the two different sets of tresses when bleach damaged and washed with 10% active SLES showed slight differences when compared to each other. Differences were expected between tresses and the observed difference was relatively small so did not give cause for concern.

On treating the tresses with the commercial conditioner of Comparative Example B, the swing height increased from 77 to 208 pixels, which relates to a 2.7 fold increase based on the untreated hair. At a resolution of 1600×900 pixels, 3.8 pixels are equal to 1 mm.

The second set of tresses was treated with Example 10 as the conditioning agent. The swing height of these tresses increased by almost 4.5 times (4.48 fold increase), from 60 to 269 pixels. These results demonstrate that the formulation of Example 10 is able to significantly improve hair movement compared to an optimised, fully formulated conditioning system containing cationic conditioning agents and silicone derivatives.

Figure 2:
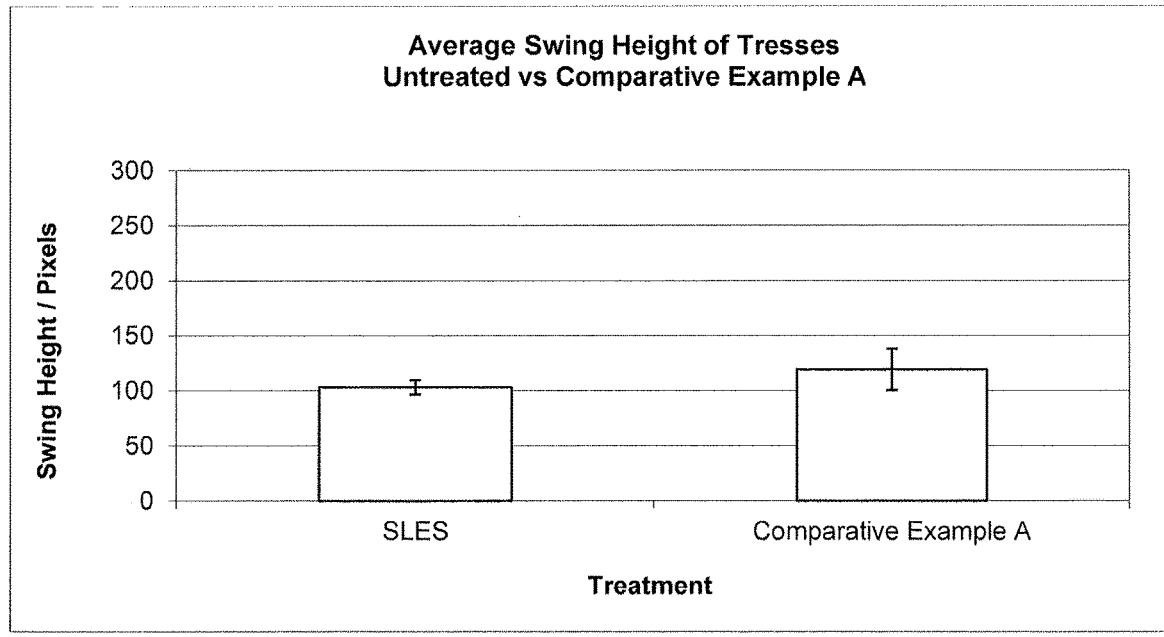
FIG. 2 is a graph of the calculated swing height of bleach damaged tresses washed with SLES only compared to tresses conditioned with Comparative Example A.

As a control, the formulation of Comparative Example A was applied to bleach damaged hair and tested for its efficacy in improving hair movement. The results are shown in FIG. 2. The observed swing heights of the products were as follows in Table 11.

TABLE 11

| Observed swing heights Treatment | |
|---|---|
| SLES | Comparative Example A |
| 103 | 119 |

The swing heights recorded for Comparative Example A demonstrate that it did not have a significant effect on the hair's movement (P>0.1) and therefore the performance seen from Example 10 can be attributed to the active material of Example 2 alone.

In addition to the swing height results, the sensory feel of the tresses was noted both before and after treatment with the respective conditioners. In each case, Comparative Example B and Example 10 altered the feel of the untreated tresses from a dry and rough feeling to a smoother, softer feel.

Example 14

Wet Combing Test

Combing tests were performed using a DiaStron MTT 175 (DiaStron Ltd, Andover, Hampshire, UK) combing machine with the comb attachment.

Materials

For cleansing hair, a 10% active Sodium Lauryl ether Sulphate (SLES) solution was prepared by diluting 35.7 g Empicol ESB/3 (Sodium lauryl ether sulphate, 28% active as supplied) in deionised water and made up to 100 g.

Results and Discussion

Figure 3:
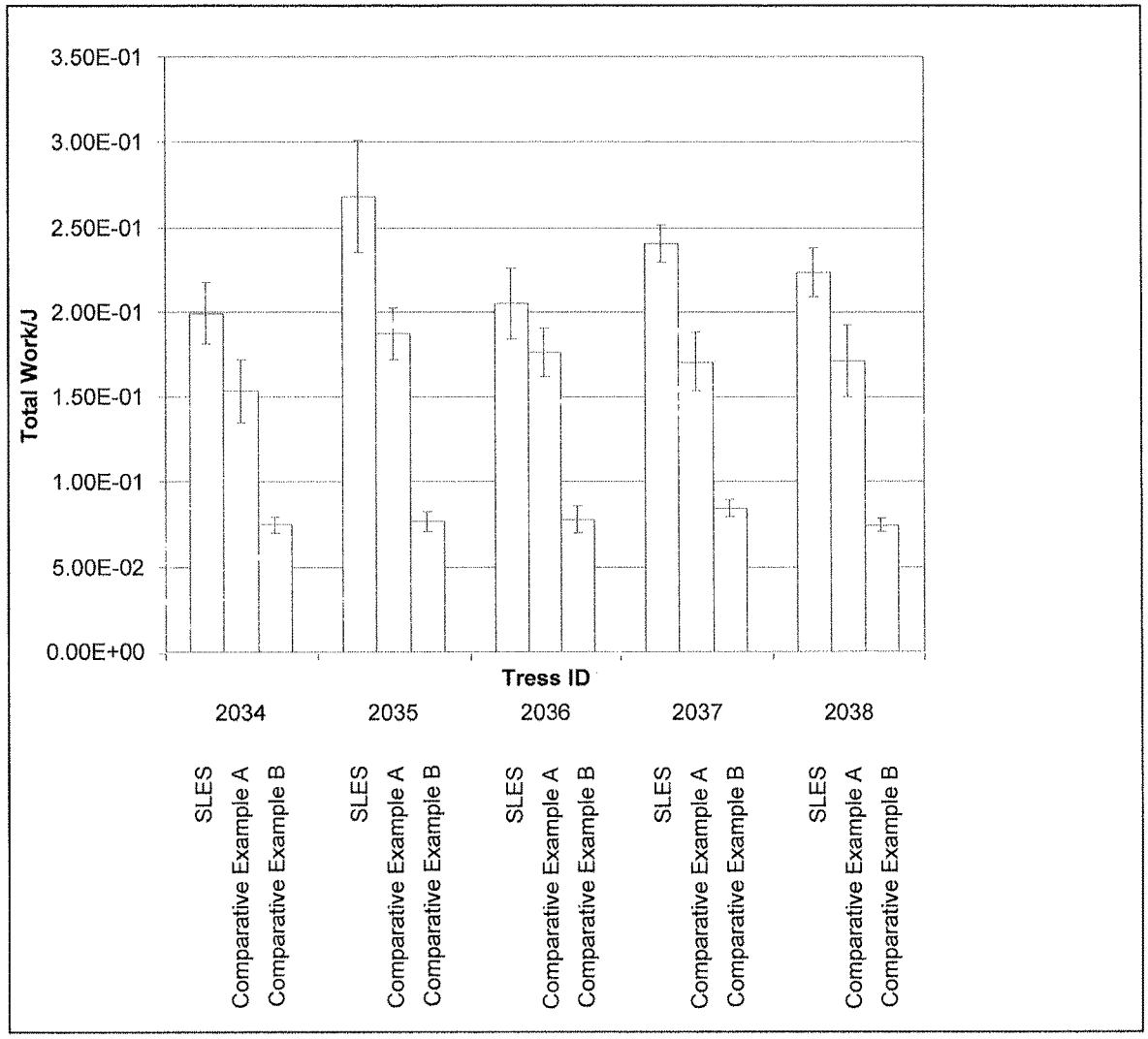
FIG. 3 is a graph of wet combing data for five tresses treated successively with SLES, Comparative Example A and the commercial conditioner formulation of Comparative Example B.
Figure 4:
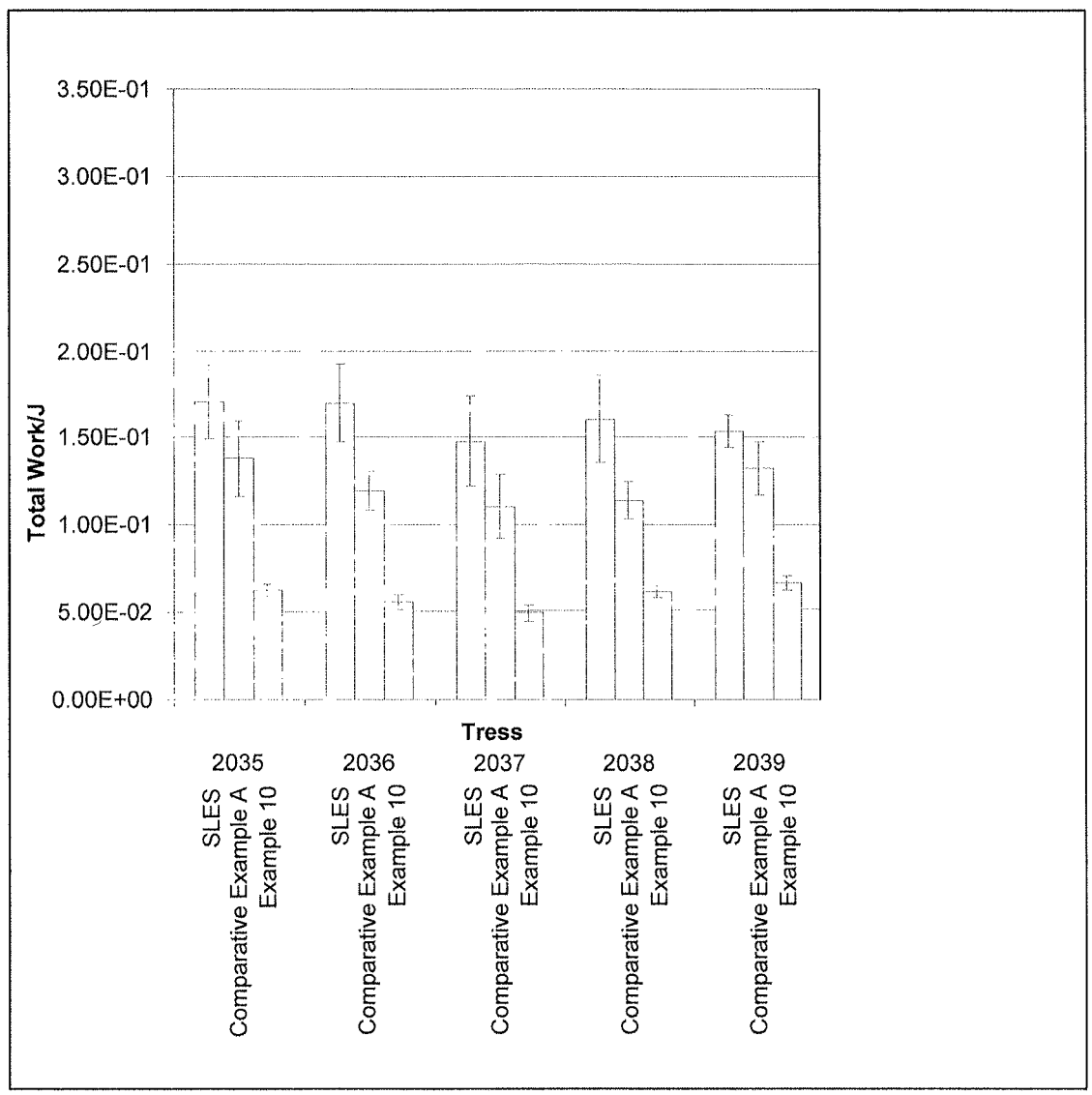
FIG. 4 is a graph of wet combing data for five tresses treated successively with SLES, Comparative Example A and the formulation of Example 10.

The wet combing data for the formulation of Example 10 is represented below as a reduction in combing force compared to both a non-conditioning treatment (SLES wash) and Comparative Examples A and B. In each case, 5 individual tresses were combed 5 times for each successive treatment and the average force taken. The results are shown in FIGS. 3 and 4. Each bar in the Figures represents the average of 5 combing results (except where outliers had been identified and removed) and the standard deviation is represented by the associated error bars.

The results in FIG. 3 show a 26.4% reduction in combing force between the SLES treatment and Comparative Example A, and an overall average combing force reduction between SLES and treatment with Comparative Example B of 66.3% which was significant at the 1% confidence interval ($p<0.001$).

The reduction caused by Comparative Example A is not unexpected as although it does not contain any conventional conditioning ingredients such as cationic conditioners or silicones, the lipophillic ingredients such as mineral oil and fatty alcohols may, in part, remain on the hair's surface after rinsing, resulting in the observed reduction in combing force.

After treatment and testing of Comparative Example A, the tresses were re-washed with the SLES solution to remove any of the lipophillic materials which may have remained on the hair's surface. This ensures that any combing force improvement seen after subsequent washing with Comparative Example B was due to this conditioner alone and not in part due to the base conditioner vehicle.

Comparative Example B was seen to give a reduction in combing force greater than that seen from Comparative Example A. This is an expected result as the product is sold commercially for its hair conditioning properties and it contains ingredients known to be substantive to the hair and to reduce hair friction.

The results in FIG. 4 again show a reduction in combing force between the SLES treatment and Comparative Example A of 25.6%, and total reduction compared to the SLES treatment upon treatment with the formulation of Example 10 of 64.9%. This percentage reduction was significant at the 1% confidence level ($p<0.001$).

The formulation of Example 10 was seen to give a reduction in combing force greater than that seen from the Comparative Examples A and B. The extent to which Example 10 reduced the combing force was surprising as this ingredient is neither quaternised nor a silicone derivative.

The present invention provides a personal care formulation with beneficial properties not seen by prior art formulations. In particular, the formulation of the invention is effective in hair care applications in enabling the hair to move freely over itself and other surfaces.

This reduction in friction experienced by the hair is instrumental in allowing the hair to move in a free way, thus promoting a healthy look and freedom of movement to the hair.

Any or all of the disclosed features, and/or any or all of the steps of any method or process described, may be combined in any combination.

Each feature disclosed herein may be replaced by alternative features serving the same, equivalent or similar purpose. Therefore, each feature disclosed is one example only of a generic series of equivalent or similar features.

The above statements apply unless expressly stated otherwise. The term specification, for these purposes, includes the description and any accompanying claims, abstract and drawings.

The invention claimed is:

1. A hair care formulation comprising an active compound which is the reaction product of a fatty acid, which is a branched carboxylic acid having a long carbon chain of 16 to 26 carbon atoms and alkyl side branches having less than 3 carbon atoms, and a polyamine having the general structure of formula I:

(Formula I)

wherein:
each $R^1$ is an —H;
each $R^2$ is independently selected from the group consisting of a methylene moiety, an ethylene moiety, a propylene moiety, and a butylene moiety;
X is —$NH_2$;
Y is H; and
n is an integer between 4 and 20,
the mol ratio of fatty acid to polyamine in the reaction product is at least 2:1,
the reaction product comprises more than one cyclic amidine moiety, and
the polyamine has a molecular weight of up to 1000 Daltons.

2. The hair care formulation of claim 1, wherein the fatty acid has a molecular weight of between 150 and 500 Daltons.

3. The hair care formulation of claim 1, wherein the polyamine has a molecular weight of at least 50 Daltons and up to 1000 Daltons.

4. The hair care formulation of claim 1, wherein the polyamine is a linear polyamine.

5. The hair care formulation of claim 1, wherein the polyamine has a general formula $NH_2(CH_2CH_2NH)_nH$, wherein n is an integer between 4 and 20.

6. The hair care formulation of claim 1, wherein the reaction product comprises symmetric compounds.

7. The hair care formulation of claim 1, wherein the active compound is present in the formulation at a concentration of at least 0.01% w/w based on the total weight of the formulation and up to 5% w/w based on the total weight of the formulation.

8. A compound for hair care comprising the reaction product of a fatty acid and a polyamine,
wherein the fatty acid is a branched carboxylic acid having a long carbon chain of 16 to 26 carbon atoms and alkyl side branches having less than 3 carbon atoms, and
wherein the polyamine has the general structure of formula I:

(Formula I)

wherein:
  each $R^1$ is an —H;
  each $R^2$ is independently selected from the group consisting of a methylene moiety, an ethylene moiety, a propylene moiety, and a butylene moiety;
  X is —$NH_2$;
  Y is H; and
  n is an integer between 4 and 20,
  the mol ratio of fatty acid to polyamine in the reaction product is at least 2:1,
  the reaction product comprises more than one cyclic amidine moiety, and
  the polyamine has a molecular weight of up to 1000 Daltons.

9. A method of reducing hair-fibre surface friction, the method comprising applying to the hair of an individual an effective amount of the hair care formulation according to claim 1.

10. The hair care formulation of claim 1, wherein the polyamine is an alkyleneamine.

11. The hair care formulation of claim 10, wherein the alkyleneamine is an ethyleneamine.

12. The hair care formulation of claim 1, wherein the fatty acid is isostearic acid and wherein the polyamine is represented by the formula $NH_2(CH_2CH_2NH)_nH$, wherein n is 4.

13. The compound for hair care of claim 8, wherein the fatty acid is isostearic acid and wherein the polyamine is represented by the formula $NH_2(CH_2CH_2NH)_nH$, wherein n is 4.

* * * * *